United States Patent
March et al.

(10) Patent No.: US 6,980,842 B2
(45) Date of Patent: *Dec. 27, 2005

(54) OCULAR ANALYTE SENSOR

(75) Inventors: Wayne Front March, Galveston, TX (US); Mary Flowers Mowery-McKee, Alpharetta, GA (US)

(73) Assignee: Novartis, Basel (CH)

( * ) Notice: Subject to any disclaimer, the term of this patent is extended or adjusted under 35 U.S.C. 154(b) by 450 days.

This patent is subject to a terminal disclaimer.

(21) Appl. No.: 10/269,394

(22) Filed: Oct. 11, 2002

(65) Prior Publication Data

US 2003/0045783 A1 Mar. 6, 2003

Related U.S. Application Data

(63) Continuation of application No. 09/901,886, filed on Jul. 6, 2001, now abandoned, which is a continuation-in-part of application No. 09/784,471, filed on Feb. 15, 2001, now Pat. No. 6,681,127, and a continuation-in-part of application No. PCT/EP00/08285, filed on Aug. 24, 2000.
(60) Provisional application No. 60/185,980, filed on Mar. 1, 2000, and provisional application No. 60/150,792, filed on Aug. 26, 1999.

(51) Int. Cl.⁷ ................................. A61B 5/00
(52) U.S. Cl. ........................ 600/319; 600/321
(58) Field of Search .................. 600/310, 318, 600/319, 316, 317, 321

(56) References Cited

U.S. PATENT DOCUMENTS

| | | | | |
|---|---|---|---|---|
| 4,987,065 A | * | 1/1991 | Stavrianopoulos et al. | 435/5 |
| 5,929,033 A | * | 7/1999 | Tang et al. | 514/12 |
| 6,120,460 A | * | 9/2000 | Abreu | 600/558 |
| 6,214,566 B1 | * | 4/2001 | Asa et al. | 435/7.1 |

* cited by examiner

Primary Examiner—Matthew J Kremer
(74) Attorney, Agent, or Firm—Jian S. Zhou; Robert J. Gorman

(57) ABSTRACT

An ophthalmic lens comprising a receptor moiety can be used to determine the amount of an analyte in an ocular fluid. The receptor moiety can bind either a specific analyte or a detectably labeled competitor moiety. The amount of detectably labeled competitor moiety which is displaced from the receptor moiety by the analyte is measured and provides a means of determining analyte concentration in an ocular fluid, such as tears, aqueous humor, or interstitial fluid. The concentration of the analyte in the ocular fluid, in turn, indicates the concentration of the analyte in a fluid or tissue sample of the body, such as blood or intracellular fluid.

25 Claims, 6 Drawing Sheets

OCULAR ANALYTE SENSOR

RELATED APPLICATIONS

Figure 1:
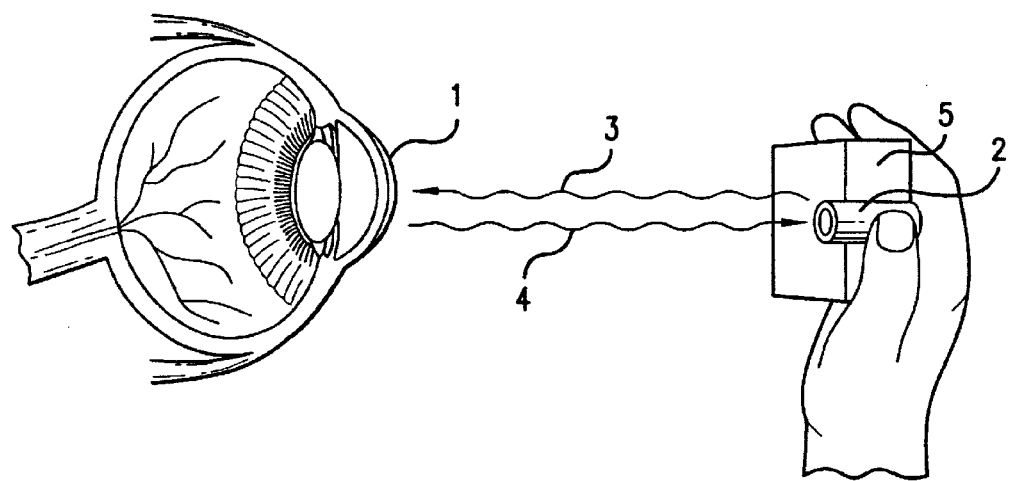
Figure 1A:
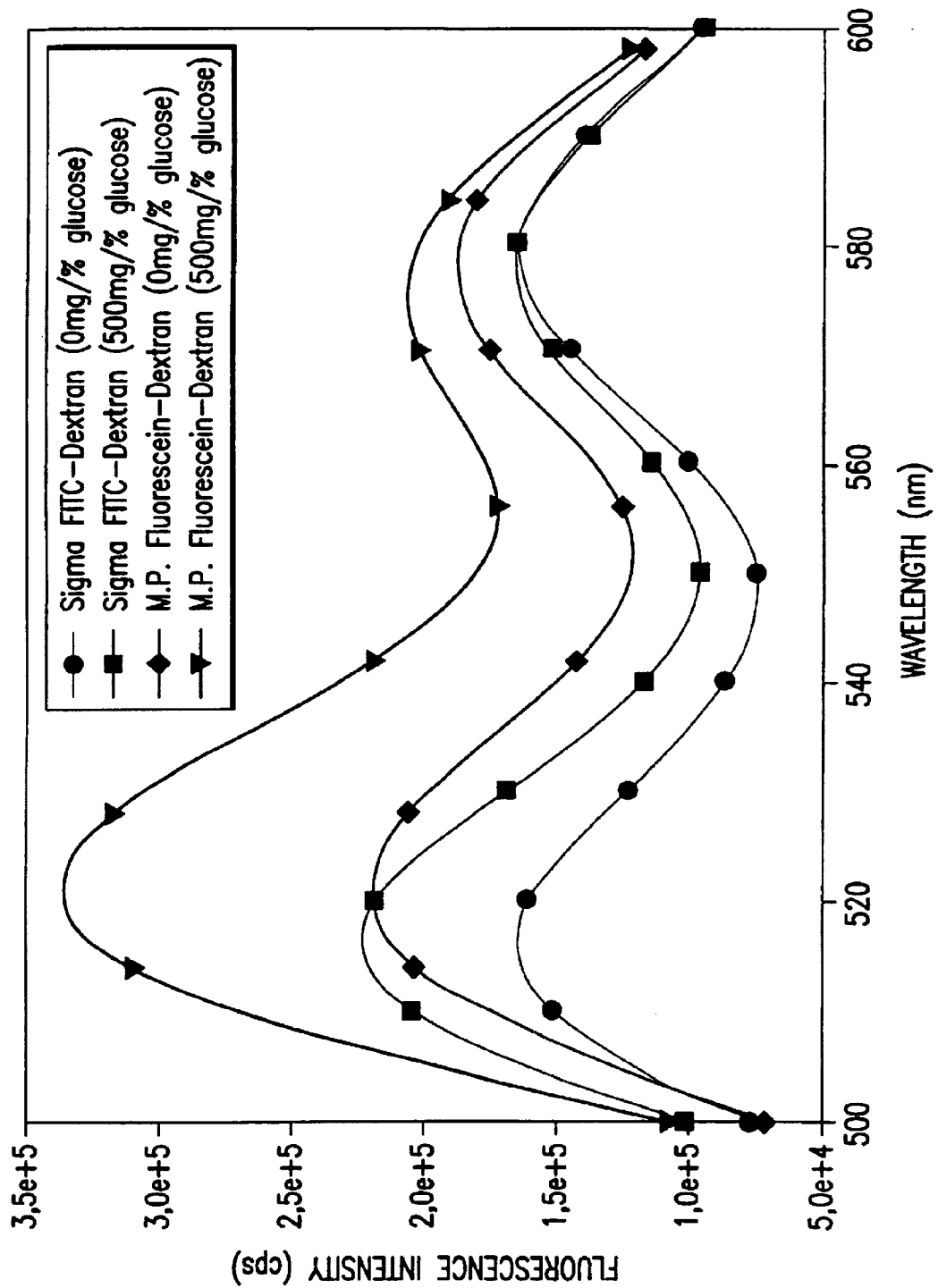

This application is a continuation of U.S. application Ser. No. 09/901,886, filed on Jul. 6, 2001, now abandoned which is a continuation-in-part of U.S. application Ser. No. 09/784,471, filed on Feb. 15, 2001, now U.S. Pat. No. 6,681,127 which claims the benefit under 35 U.S.C. 119(e) of U.S. provisional application Ser. No. 60/185,980 filed on Mar. 1, 2000 and is also a continuation-in-part of a PCT application PCT/EP00/08285, filed on Aug. 24, 2000, which claims the priority of U.S. provisional application Ser. No. 60/150,792, filed on Aug. 26, 1999 and U.S. provisional application Ser. No. 60/185,980, filed on Mar. 1, 2000.

FIELD OF THE INVENTION

An ophthalmic lens comprising a receptor moiety can be used to determine the amount of an analyte in an ocular fluid which is accessible to light. The receptor moiety can bind either a specific analyte or a detectably labeled competitor moiety. The amount of detectably labeled competitor moiety which is displaced from the receptor moiety by the analyte is measured and provides a means of determining analyte concentration in an ocular fluid, such as tears, aqueous humor, or interstitial fluid. The concentration of the analyte in the ocular fluid, in turn, indicates the concentration of the analyte in a fluid or tissue sample of the body that is not as accessible, such as blood or intracellular fluid.

BACKGROUND OF THE INVENTION

Various noninvasive or minimally invasive methods to measure analytes, particularly glucose, have been described. For example, March, U.S. Pat. Nos. 3,958,560 and 4,014,321, discloses a glucose sensor wherein a patient's eye is automatically scanned using a source of light at one side of the cornea. A sensor located at the other side of the cornea detects the light that passes through the cornea. The level of glucose which rotates the plan of polarized light in the aqueous humor of the patient is a function of the amount of radiation detected. However, this sensor system is not necessarily specific or widely applicable to detection of analytes other than glucose, because it does not exploit the use of biological molecules which can detect glucose or other analytes in a body tissue or fluid sample. Biological molecules, as is well known, can provide very specific and sensitive detection reagents for particular analytes.

Schultz, U.S. Pat. No. 4,344,438, discloses a system for monitoring low molecular weight compounds in blood plasma by optical means, which involves a chamber which contains specific receptor sites for the plasma constituent to be analyzed. This system is very invasive, however, because it must be implanted within the blood stream using a hypodermic needle. The system also inherently contains the risks of clotting around the device, obstruction, and other adverse reactions, including immune reactions, general irritation, and foreign body reactions.

SUMMARY OF THE INVENTION

Embodiments of the present invention overcome these disadvantages in the prior art by employing an ophthalmic lens comprising a receptor moiety which comprises an analyte/competitor moiety binding site to detect an analyte in an ocular fluid. Concentration of a wide variety of analytes can be measured using an ophthalmic lens according to embodiments of the invention. Such analytes include, but are not limited to, electrolytes and small molecules (e.g., sodium, potassium, chloride, phenylalanine, uric acid, galactose, glucose, cysteine, homocysteine, calcium, ethanol, acetylcholine and acetylcholine analogs, ornithine, blood urea nitrogen, creatinine), metallic elements (e.g., iron, copper, magnesium), polypeptide hormones (e.g., thyroid stimulating hormone, growth hormone, insulin, luteinizing hormones, chorionogonadotrophic hormone), chronically administered medications (e.g., dilantin, phenobarbital, propranolol), acutely administered medications (e.g., cocaine, heroin, ketamine), small molecule hormones (e.g., thyroid hormones, ACTH, estrogen, cortisol, estrogen, and other metabolic steroids), markers of inflammation and/or allergy (e.g., histamine, IgE, cytokines), lipids (e.g., cholesterol), plasma proteins and enzymes (e.g., complement, coagulation factors, liver function enzymes, heart damage enzymes, ferritin), markers of infection (e.g., virus components, immunoglobulins such as IgM, IgG, etc., proteases, protease inhibitors), and/or metabolites (e.g., lactate, ketone bodies).

Ophthalmic lenses according to embodiments of the invention can be used to monitor the course of therapy or the level of disease in mammals, including primates and, preferably, humans. In addition, because ophthalmic lenses according to embodiments of the invention provide a way to detect analytes noninvasively, they provide distinct advantages over more traditional forms of monitoring such levels. Ophthalmic lenses according to embodiments of the invention also are useful for diagnostic purposes, for example to test for pregnancy (to detect β-HCG), to assess blood chemistry (electrolytes, $Ca_2PO_4$, magnesium, bilirubin, alkaline phosphatase, lactate dehydrogenase, alanine aminotransferase, etc.), and to detect infection (e.g., by detecting components of viruses such as CMV, EBV, hepatitis, and HIV, or bacteria, such as Staphlococcus, Streptococcus, etc.). They also are useful for monitoring blood levels of test compounds during the course of assessing the compounds for use as potential therapeutics.

Ophthalmic lenses according to embodiments of the invention can be worn chronically to provide repeated analyte measurements or can be worn for a single analyte measurement. Both qualitative and quantitative measurements can be performed.

DETAILED DESCRIPTION OF THE PREFERRED EMBODIMENTS

Ophthalmic Lens

An ophthalmic lens according to embodiments of the invention can be a removable lens, such as a contact lens, or a permanently implanted lens, such as an intraocular lens, a subconjunctival lens, or an intracorneal lens. See U.S. Ser. Nos. 60/150,792 and 60/185,980, the patent applications the priority of which is claimed for this invention. Permanently implanted lenses are particularly well-suited for use in individuals who have compromised ocular function (e.g., cataracts) and also have chronic conditions which require analyte measurement, such as diabetics.

Ophthalmic lenses can be corrective lenses or can be constructed so that they do not affect visual acuity. Contact lenses optionally can comprise a tint and are preferably disposable, which reduces the risk of infection for the user. As used herein, the term "ophthalmic lens" may also refer to a shunt or implant that may rest in the cul de sac of the eye.

Receptor Moiety

The ophthalmic lens comprises a receptor moiety. The receptor moiety comprises a binding site for the analyte to be detected. The binding site also binds a moiety which competes with the analyte for binding and is therefore referred to herein as an "analyte/competitor moiety binding site." Binding of both the competitor moiety and the analyte to the analyte/competitor moiety binding site is reversible. The nature of the molecule used as the receptor moiety depends on the particular analyte to be detected, but minimally includes that portion of the molecule which is sufficient to contain an analyte/competitor moiety binding site.

For example, if glucose is the analyte to be detected, the receptor moiety preferably is concanavalin A (Mansouri & Schultz, *Bio/Tech* 2, 385, 1984) or glucose oxidase, although other moieties, such as antibodies, boronic acid, or a genetically engineered bacterial fluoriprotein, also can be used.

Boronic acid derivatives may also be used as competitive moieties for glucose, as they form covalent complexes with glucose. For example, a combination of a fluorescence moiety, such as anthracene, boronic acid and tertiary amine gives a sensor for glucose. Illustrative, but none limiting boronic acid compounds are listed below:

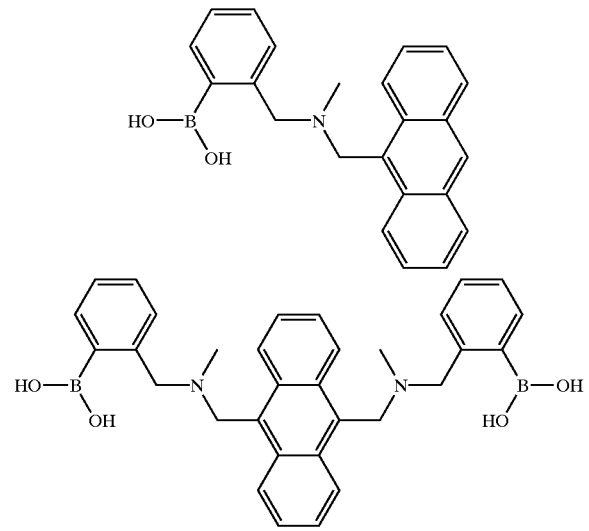

Glucose binds with the acidic boronic moiety creating a fluorescent moiety.

If phenylalanine is the analyte to be detected, the receptor moiety preferably comprises the active site of phenylalanine hydroxylase. It is well within the skill of those knowledgeable in the art to determine other analyte-receptor moiety binding pairs, such as uric acid-uricase, alcohol-alcohol dehydrogenase, copper-ceruloplasmin, galactose-galactokinase, cysteine- and/or homocysteine-cystathionine synthetase, acetylcholine-acetylcholinesterase, ornithine-diamine oxidase, and the like.

Competitor Moiety

For use in detecting an analyte, an ophthalmic lens according to embodiments of the invention preferably comprises a competitor moiety having a detectable label. The competitor moiety competes with the analyte for binding to the analyte/competitor moiety binding site. The detectable label can intrinsically be part of the competitor moiety. Alternatively, the detectable label can be a label which is not naturally associated with the competitor moiety but which is attached by means of a chemical linkage, such as a covalent bond. In preferred embodiments, the competitor moiety comprises a fluorescent label. Other detectable labels, such as luminescent or colorimetric labels, also can be used.

Again, it is well within the skill of those in the art to select a competitor moiety which will compete with an analyte for binding to a particular analyte/competitor moiety binding site. For example, competitor moieties which can be used with the analyte-receptor moiety binding pairs disclosed above include fluorescein dextran (which competes with glucose for binding to concanavalin A), 2-deoxy-D-glucose or D-mannose or D-galactose (which competes with glucose for binding to glucose oxidase), fluorescein polyglutamylurate (which competes with uric acid for binding to uricase), fluorescein nanolol (which competes with alcohol for binding to alcohol dehydrogenase), fluorescein-glutamine phenylacetate (which competes with phenylalnine for binding to phenylalanine hydroxylase), fluorescein-erythrocuprein (which competes with copper for binding to ceruloplasmin), fluorescein-2,3,6-tri-O-methyl galactose (which competes with galactose for binding to galactokinase), fluorescein-S-adenosyl polyhomocysteine (which competes with cysteine and homocysteine for binding to cystathionine synthetase), fluoropolyglutamyl prostigmine (which competes with acetylcholine for binding to acetylcholinesterase), and fluorospermine (which competes with ornithine for binding to diamine oxidase).

Most preferably, the detectable label is more readily detectable when the competitor moiety is not bound to the analyte/competitor moiety binding site. Thus, fluorescent labels, such as fluorescein, indocyanine green, malachite green, rhodamine, Alexa Fluor® dyes (e.g., Alexa 488), Oregon Green® dyes (e.g., Oregon Green 488), BODIPY (4,4-difluoro-4-bora-3a,4a-diaza-s-indacene) fluorophores, cyanine dyes (e.g., Cy2), and phycobiliproteins, which are quenched when the competitor moiety is bound but are unquenched when the competitor moiety is not bound, are preferred for use in ophthalmic lenses according to embodiments of the invention.

In addition, the sensitivity of the monitor can be controlled by altering the concentration of the detectable label. For example, the free resonance energy transfer function, an indicator of measurement sensitivity, can be increased by increasing the concentration of the detectable label. Thus in the case of fluorescein dextran (which competes with glucose for binding to concanavalin A), increasing the concentration of fluorescein on the competitive moiety increases the range of fluorescence intensity. Increasing the range of fluorescence intensity increases the sensitivity of resulting measurements.

The principle is illustrated in FIG. 1. Two different fluorescein dextran compounds, each with differing fluorescein concentrations, were tested in the same glucose environments and the fluorescence intensity measured. Sigma FITC-Dextran has a fluorescein concentration of 2% and M.P. Fluorescein-Dextran has a fluorescein concentration of 4%. Each solution was measured in a fluorophotometer with variable wavelength. The first peak is characteristic of fluorescein, the second of rhodamine. As can be seen from FIG. 1, M.P. Fluorescein-Dextran, the compound with the higher fluorescein concentration has a greater range of fluorescence intensity as measured at a given wavelength than the Sigma FITC-Dextran. The larger range of fluorescence gives greater sensitivity when measuring patient glucose levels.

It is important to note the purity of the competitive moiety can influence the activity level of the detectable label. For example, in the case of fluorescein dextran, the relative level of monomers, dimers or tetramers can influence the sensitivity. Relatively pure levels of dimers seem to positively influence sensitivity.

Providing Receptor and Competitor Moieties in an Ophthalmic Lens

A variety of options are available for providing the receptor and competitor moieties in an ophthalmic lens. Construction of various types of ophthalmic lenses is well known in the art. Construction of contact lenses is taught, for example, in U.S. Pat. Nos. 5,965,631, 5,894,002, 5,849,811, 5,807,944, 5,776,381, 5,426,158, 4,099,859, 4,229,273, 4,168,112, 4,217,038, 4,409,258, 4,388,164, 4,332,922, 4,143,949, 4,311,573, 4,589,964, and 3,925,178.

Construction of intraocular lens implants is taught, inter alia, in U.S. Pat. Nos. 6,051,025, 5,868,697, 5,762,836, 5,609,640, 5,071,432, 5,041,133, and 5,007,928. Subconjunctival lenses are taught, for example, in U.S. Pat. Nos. 5,476,511, 5,400,114, and 5,127,901. Intracorneal lenses are taught, inter alia, in U.S. Pat. Nos. 6,090,141, 5,984,961, 5,123,921, and 4,799,931.

In one embodiment, the receptor moiety is covalently bound to the ophthalmic lens material. In another embodiment, the ophthalmic lens comprises a polymer meshwork containing pores. The pores are of a size which permit the competitor moiety to bind reversibly to the analyte/competitor moiety binding site, but which prevent the receptor moiety and the competitor moiety from diffusing out of the ophthalmic lens. Suitable polymers for this purpose are known in the art and include hydrogels, such as stable polymers of polyethylene glycol hydrogel (PEGH) (March et al., 2000), polyvinylalcohols (PVA), modified polyvinylalcohol (e.g., as nelfilcon A), PVAs with polycarboxylic acids (e.g., carbopol) which may contain crosslinkable functional groups, water-soluble macromer or polymers, starpolymers, dendrimers, and other biopolymers In another embodiment, the competitor moiety is tethered to a polymer meshwork containing pores. The pores are of a size which permit an analyte to bind reversibly to the analyte/competitor moiety binding site, but which prevent the receptor moiety from diffusing out of the ophthalmic lens.

The receptor can be covalently linked to a polymer meshwork according to any known, suitable methods. A polymer meshwork can comprise or be modified to comprise reactive moieties such as groups containing amine, hydroxy, isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, acid halide, hydroxysuccinimide ester, hydroxysulfosuccinimide ester, imido ester, hydrazine, axidonitrophenyl, azide, 3-(2-pyridyl dithio)proprionamide, glyoxal and aldehyde. For example, a cyclic acetate can be introduced into a PVA meshwork via an aldehyde group containing a function end-group such as an amine. The amino end-group can be modified into an isocyanate or isothiocyanate. A reactive moieties of a polymer meshwork can be reacted with a function group on the receptor moieties to form a covalent bond. Exemplary functional groups include but are not limited to amine, hydroxy and sulfhydryl.

Similarly, a competitor moiety can be tethered, preferably via a flexible linker, to a polymer meshwork according to any known, suitable methods. Introduction of flexible linkers into a polymer meshwork or a competitor moiety is known to a person skilled in the art. A flexible linker may not have significantly adverse effects on the binding affinity of the competitor moiety to the receptor moiety while eliminating the out-diffusion of the competitor moiety, especially small competitor moiety molecule.

In another embodiment, the ophthalmic lens comprises a receptor moiety layer, a polyelectrolyte layer, and a competitor moiety layer. The polyelectrolyte layer includes one or more polyelectrolytes, which are generally high molecular weight polymers with multiple ionic or ionizable functional groups. At least one polyelectrolyte in the polyelectrolyte layer has a charge opposite to the overall charge of the receptor moiety and competitor moiety layers. Suitable polyelectrolytes include positively charged PDDA (polydiallyldimethylammonium chloride) and negatively charged PAA (polyacrylic acid). Assembly of the layers is based upon sequential adsorption of oppositely charged polyions. The sensor and spacing polyelectrolytes are deposited as uniform thin films (1–10 nm) in 10–15 deposition cycles onto the porous polyvinyl alcohol or hydrogen matrix, resulting in only a 100–500 nm thick coating for the sensing film, which is highly biocompatible. A typical sequence for construction of an ophthalmic lens suitable for glucose detection involves a deposition cycle of ultrathin (1–10 nm) films of PDDA, PAA, PDDA, concanavalin A, PDDA, PAA, PDDA, fluorescein dextran, PDDA, PAA, PDDA, PAA, concanavalin A, PAA, fluorescein dextran, PAA, etc. Technology for constructing ophthalmic lenses comprising such layers is taught, for example, in WO 99/35520.

An ophthalmic lens according to embodiments of the invention can be provided in a kit, together with instructions for measuring analyte concentration as described below. The invention provides kits which are intended for individual patient use, in which the ophthalmic lens typically is a contact lens, as well as kits for medical practitioners, which can comprise any of the ophthalmic lenses or their equivalents described herein.

Analyte Sensor System

An ophthalmic lens according to embodiments of the invention can be used in an analyte sensor system. The analyte sensor system comprises an ophthalmic lens and a detector configured to detect the detectable label. For example, if the label is a luminescent label, the detector may include a luminometer; if the label is a colorimetric label, the detector may include a calorimeter; if the label is a fluorescent label, the detector may include a fluoro-photometer. Construction of such devices is well known in the art. Light with wavelengths which will excite the fluorescent label can be provided, for example, by a laser or a light source, such as a light-emitting diode. A fluorophotometer suitable for use with embodiments of the invention can be constructed using a light-emitting diode from Power Technology, Inc. (Little Rock, Ark.) (see March et al., *Diabetes Technol. & Ther.* 2, 27–30, 2000).

The detector can be a free-standing device, a table-top device, or a hand-held device. For convenience, the detector can be a miniaturized device and may be worn or carried as a personal accessory, for example, mounted in the frame of a pair of eyeglasses, clipped to an article of clothing, such as a shirt or sweater, hung around the neck, worn around the wrist, or clipped to a belt or a key ring.

Using an ophthalmic lens in an analyte sensor system, as described above, embodiments of the invention provides methods of measuring analyte concentration in an ocular fluid. This measurement can, in turn, be manipulated to provide a measurement of the analyte's concentration in a body tissue or a fluid, such as blood or intracellular fluid. The relationship between glucose concentration in the aqueous humor and the blood, for example, is well known. See Süllmann, in Handbuch Der Physiologischen Chemie, Vol. II/a, p. 867 ff., Springer, Berlin, 1956; Graymore, in The Eye, Vol. I, p. 348, Davson, ed., Academic Press, N.Y., 1962; De Berardinis et al., *Exp. Eye Res.* 4, 179, 1965; Pohjola,

*Acta Ophthalmologica Suppl.* 88, 1966; Reim et al., *Ophthalmologica* 154, 39–50, 1967; Kinsey & Reddy, in Prince, ed., The Rabbit and Eye Research, C.C. Thomas, Springfield, Ill., 1964, p. 218. The relationship between the concentration of another analyte in a body tissue or fluid and the concentration of the analyte in an ocular fluid can be determined by methods well known in the art. See, for example, March et al., *Diabetes Care* 5, 259–65, 1982. The detector can be configured to convert the measurement of the analyte concentration into a value which reflects the concentration of the analyte in the relevant body tissue or fluid, e.g., blood.

If desired, the analyte sensor system also can comprise a transmitter configured to transmit a signal representing whether the detectable label is detected and/or an amount of the detectable label that is detected. A device configured to vary the concentration of the analyte in a body fluid or tissue, such as an infusion pump or other pump, may receive the signal and may vary the concentration response to the signal. The signal from the analyte sensor system may comprise a continuous or discontinuous telemetry signal generated by the detector. The pump may, in response to the signal, adjust the levels of the analyte in the body by providing the user with the appropriate amount of a regulator moiety, such as insulin. Infusion pumps are well known in the art for delivering a selected medication to a patient including humans and other animals in accordance with an administration schedule which can be preselected or, in some instances, preprogrammed. Pumps for use in this invention can be worn externally or can be directly implanted into the body of a mammal, including a human, to deliver a specific medication such as insulin to the mammal in controlled doses over an extended period of time. Such pumps are well known and are described, for example, in U.S. Pat. Nos. 5,957,890, 4,923,375, 4,573,994, and 3,731,681. Medications which should optimally be maintained at a constant level, such as phenobarbital, baclofen, theophylline, and cardiac and blood pressure medications, also can be provided by means of an infusion pump.

Illustrative Embodiments

Illustrative embodiments of the analyte sensor system according to embodiments of the invention are shown in FIGS. 1 and 2. FIG. 1 is a schematic view of an analyte sensor system employing a contact lens 1, a radiation detector 5, such as a fluorophotometer, and a radiation source 2, such as a laser (which preferably is of low power) or light emitting diode, which emits light 3 with a first wavelength which will excite the fluorescent label in competitor moieties contained within the contact lens 1. In response to the light 3, competitor moieties which are not bound to receptor moieties will thereby emit light 4 of a second different wavelength (e.g., by fluorescence), which can be detected and measured by a radiation detector 5. The radiation detector 5 and the radiation source 2 may be embodied together as a hand-held unit, as shown in FIG. 1.

Figure 2B:
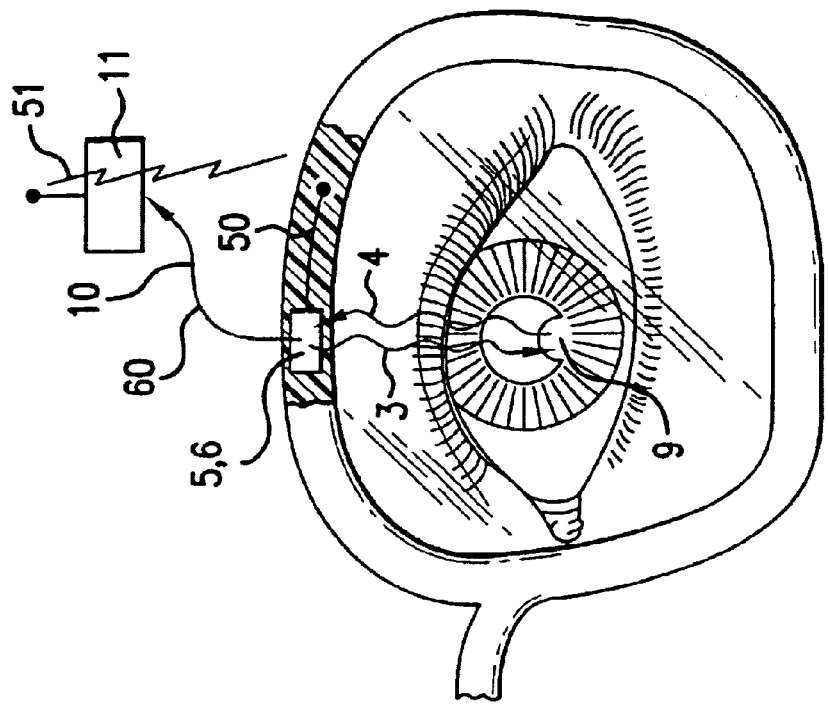
Figure 2A:
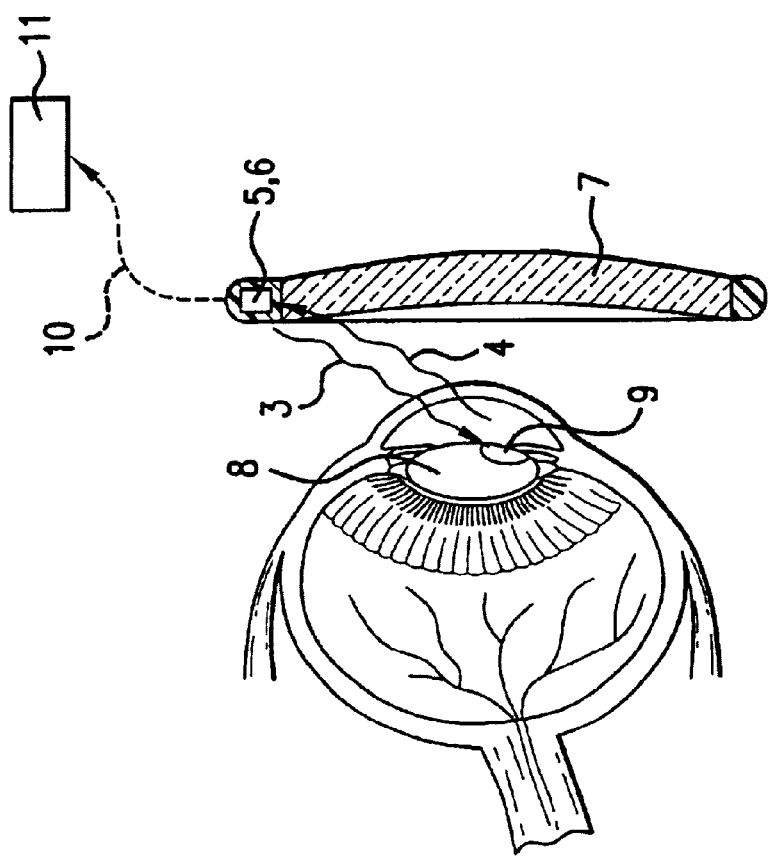
Figure 2C:
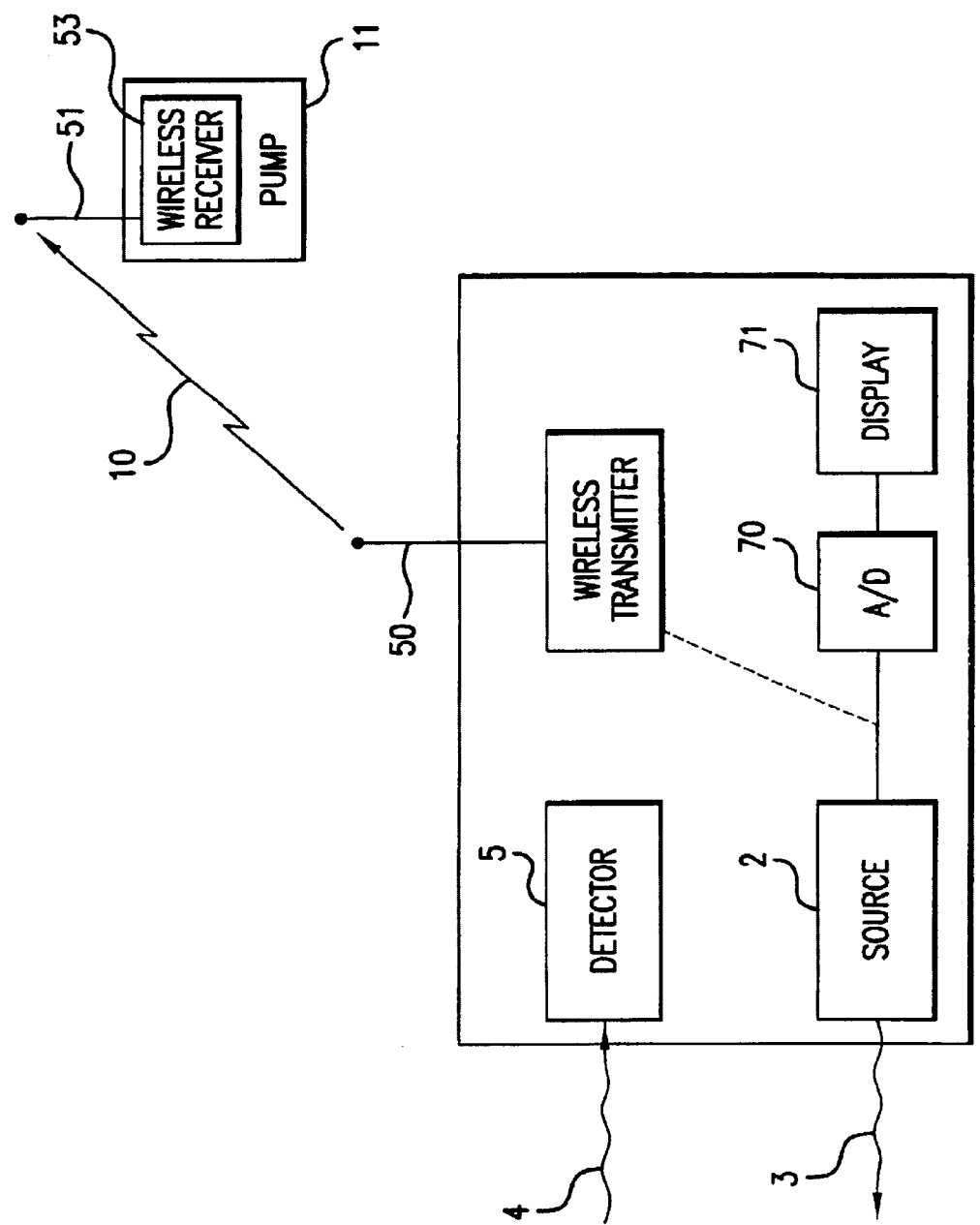
Figure 3A:
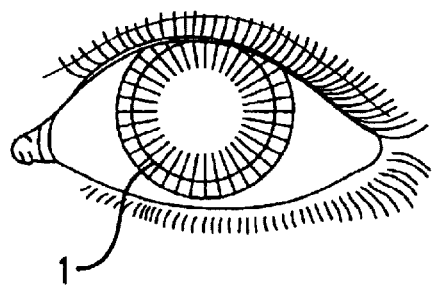
Figure 3B:
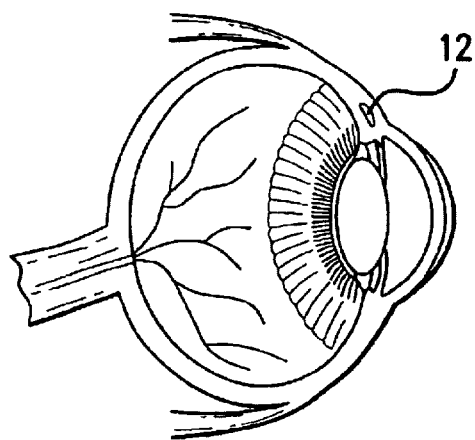
Figure 3C:
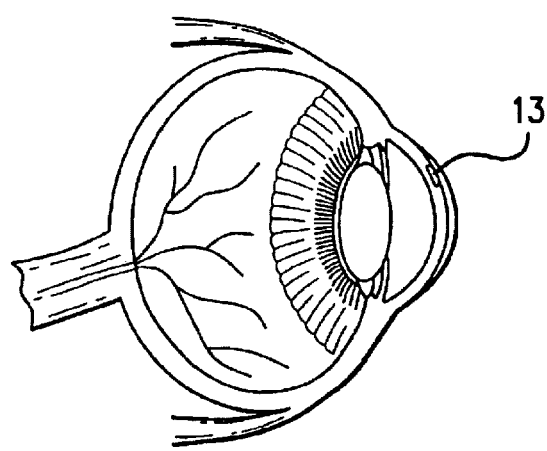

Conveniently, a miniaturized version of the radiation source 2 and the radiation detector 5 can be configured to be built into a pair of eyeglasses. An exemplary embodiment of this is shown in FIGS. 2A and 2B. The analyte sensor system shown in FIGS. 2A and 2B employs an intraocular lens 8, which comprises a polymer 9 containing receptor moieties and fluorescently labeled competitor moieties. A light-emitting diode 6 is mounted in the frame of a pair of eyeglasses 7. The light-emitting diode 6 emits light 3 with a first wavelength which will excite the fluorescent label in the competitor moieties. Competitor moieties which are not bound to receptor moieties will thereby emit light 4 of a second different wavelength, which can be detected and measured by a fluorophotometer 5, which is mounted together with the light-emitting diode 6 in the eyeglasses frame 7. A telemetry signal 10 is transmitted to an infusion pump 11, which can provide a regulator moiety, such as insulin, to maintain suitable levels of the analyte in the body. The telemetry signal 10 may be analog or digital and may be transmitted via wire or cable, such as wire 60, or wirelessly, such as via radio frequency or infrared transmission. Where the telemetry signal 10 is transmitted wirelessly, the analyte sensor system may include antennas 50, 51, for such wireless transmission. Antenna 50 may, if desired, be embedded within eyeglass frame 7. As shown in FIG. 2C, the antennas 50, 51 may be coupled with a respective wireless transmitter 52 and wireless receiver 53.

The telemetry signal 10 may include qualitative information as to whether or not the analyte is detected by the radiation detector 5. For example, where the detected light 4 is at or exceeds a predetermined threshold, the telemetry signal 10 may represent a "detected" state (such as the existence of telemetry signal 10). Where the detected light 4 is below the threshold, the telemetry signal 10 may represent a "not detected" state (such as the absence of telemetry signal 10). Alternatively, the telemetry signal 10 may indicate a change in analyte concentration. Telemetry signal 10 also may provide a warning signal if the analyte concentration is above or below a preset range.

Optionally, the telemetry signal 10 may include quantitative information as to how much light 4 is detected by the radiation detector 5. For instance, the telemetry signal 10 may be varied in amplitude and/or frequency responsive to the amount of light 4 detected, where the amplitude and/or frequency represents the amount of light 4. As another example, the telemetry signal 10 may include digital data representing the amount of detected light 4.

If the telemetry signal 10 is analog, the telemetry signal 10 may be generated by the detector 5, which may include a modulator for generation of the telemetry signal 10. If the telemetry signal 10 is digital, the telemetry signal 10 may be generated by an analog-to-digital ("A/D") converter 70. Also, the amount of the light 4 detected by the radiation detector 5 may be shown on a display 71 (which may include a display driver), such as a CRT screen or liquid crystal display ("LCD").

All patents and patent applications cited in this disclosure are expressly incorporated herein by reference. The above disclosure generally describes the present invention. A more complete understanding can be obtained by reference to the following specific examples which are provided for purposes of illustration only and are not intended to limit the scope of the invention.

EXAMPLE 1

Construction of an Intraocular Glucose Sensor

A structurally stable polymer of polyethylene glycol hydrogel (PEGH, Shearwater Polymers, Inc.) is used to construct an intraocular glucose sensor. PEGH is immobilized in an intraocular lens (Alcon Laboratories, 6 mm circumference, 1 mm thickness). Chemically immobilized pendant tetramethylrhodamine isothiocyanate concanavalin A (TRITC-ConA, Sigma) is incorporated into the PEGH as the receptor moiety and fluorescein isothiocyanate dextran (FITC-dextran, Sigma) is incorporated as the competitor moiety by polymerization under UV light, as described by Ballerstadt & Schultz, *Anal. Chim. Acta* 345, 203-12, 1997, and Russell & Pishko, *Anal. Chem.* 71, 3126-32, 1999. While the FITC-dextran is bound to the TRITC-ConA, the FITC fluorescence is quenched via a fluorescence resonance energy transfer. Increased glucose concentration frees the FITC-dextran and results in fluorescence which is proportional to glucose concentration.

Figure 4:
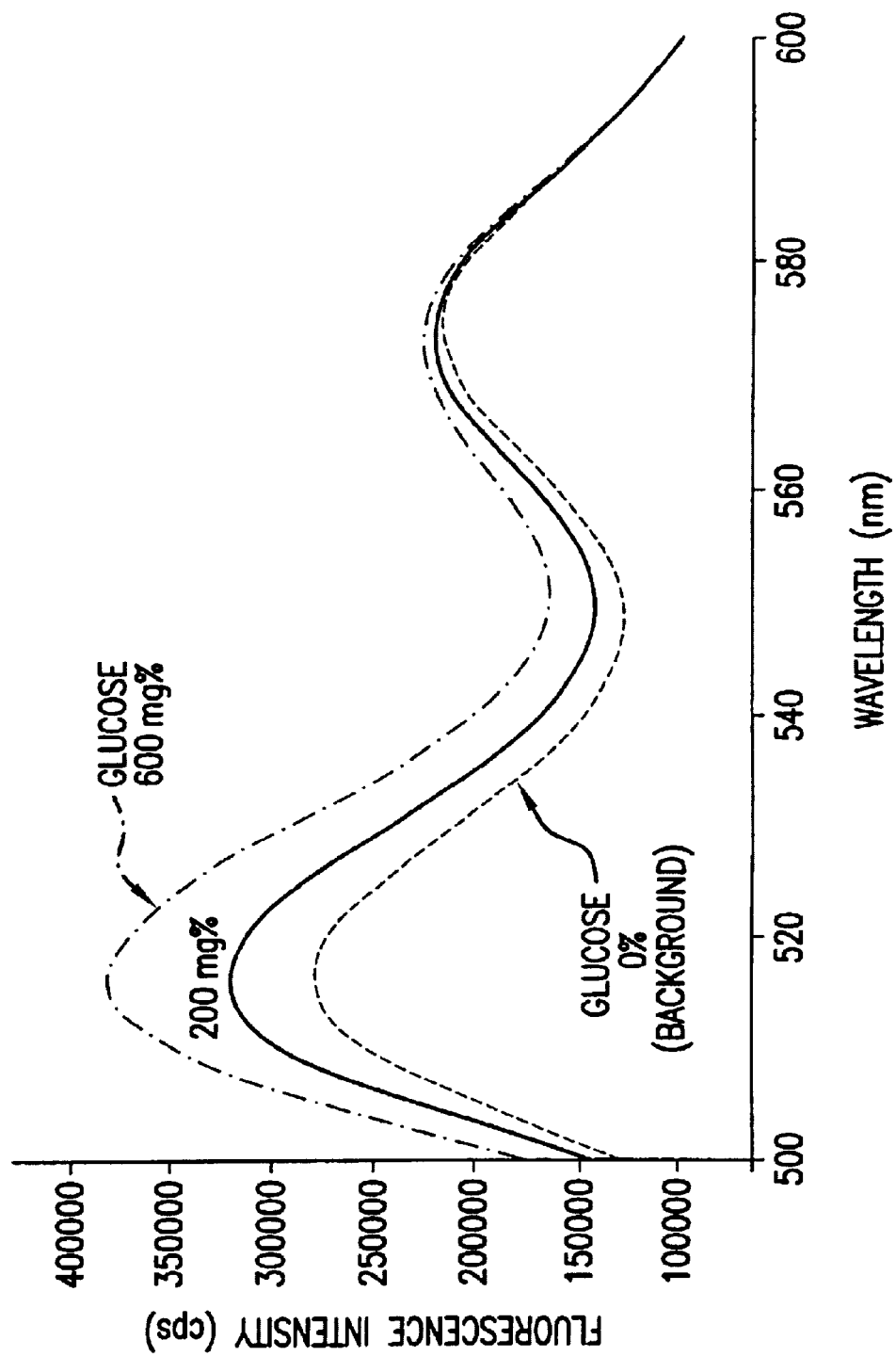

FIG. 4 shows the relationship between fluorescence intensity of our fluorescent intraocular lens at three glucose concentrations in vitro. A linearly proportional relationship occurs between 0 and 500 mg % at 518 nm, which is the peak of fluorescein fluorescence. The peak at 575 nm is due to the rhodamine in the TRITC-ConA.

EXAMPLE 2

Implantation of an Intraocular Glucose Sensor in vivo

The intraocular lens glucose sensor described in Example 1 is implanted into the anterior chamber of the eye of a living New Zealand rabbit with a blood glucose concentration of 112 mg %. The implant is visible as a bright spot of green fluorescence (518 nm) within the eye. Careful examination with a biomicroscope slit lamp shows no sign of toxicity, rejection, or any reaction 6 months after implantation.

What is claimed is:

1. An ophthalmic lens for detecting glucose in an ocular fluid, comprising:

competitor moieties;

glucose oxidase molecules comprising glucose/competitor moiety binding sites to which glucose and competitor moieties can reversibly bind; and detectable labels which are associated with the glucose oxidase molecules and/or the competitor moieties and which are capable of generating an optical signal that changes in a concentration-dependent manner when glucose reversibly binds to the glucose/competitor moiety binding sites.

2. An ophthalmic lens of claim 1, wherein the competitor moieties are selected from the group consisting of 2-deoxy-D-glucose, D-mannose and D-galactose.

3. An ophthalmic lens of claim 2, wherein the competitor moieties are tethered to a polymer meshwork, wherein pores of the polymer meshwork (a) permit glucose to bind reversibly to the glucose/competitor moiety binding sites and (b) prevent the glucose oxidase molecules from diffusing out of the ophthalmic lens.

4. An ophthalmic lens of claim 1, wherein at least one of the detectable labels is a fluorescent label.

5. A glucose sensor system, comprising:

an ophthalmic lens for detecting glucose in an ocular fluid, wherein the ophthalmic lens includes competitor moieties, glucose oxidase molecules having glucose/competitor moiety binding sites to which glucose and the competitor moieties can reversibly bind, and detectable labels which are associated with the glucose oxidase molecules and/or the competitor moieties and which are capable of generating an optical signal that changes in a concentration-dependent manner when glucose reversibly binds to the glucose/competitor moiety binding sites; and a detector configured to detect the optical signal.

6. A glucose sensor system of claim 5, wherein the competitor moieties are selected from the group consisting of 2-deoxy-D-glucose, D-mannose and D-galactose.

7. A glucose sensor system of claim 6, wherein the competitor moieties are tethered to a polymer meshwork, wherein pores of the polymer meshwork (a) permit glucose to bind reversibly to the glucose/competitor moiety binding sites and (b) prevent the glucose oxidase molecules from diffusing out of the ophthalmic lens.

8. A glucose sensor system of claim 5, wherein the detector is a fluorophotometer.

9. A glucose sensor system of claim 5, further comprising an insulin pump and a transmitter coupled to the detector and configured to transmit to the insulin pump a signal indicating a glucose concentration in the ocular fluid, wherein the pump is configured to vary the level of glucose in a body fluid or tissue according to the glucose concentration in the ocular fluid.

10. A glucose sensor system of claim 9, wherein the transmitter is contained in a personal accessory.

11. A glucose sensor system of claim 10, wherein the transmitter is further configured to transmit the signal to the insulin pump wirelessly.

12. A glucose sensor system of claim 5, wherein the ophthalmic lens is selected from the group consisting of a contact lens, an intraocular lens, a subconjunctival lens, and an intracorneal lens.

13. A method for measuring glucose concentration in an ocular fluid, comprising the steps of:

contacting the ocular fluid with an ophthalmic lens, wherein the ophthalmic lens comprises competitor moieties, glucose oxidase molecules each of which comprises a glucose/competitor moiety binding site to which glucose and competitor moieties can reversibly bind, and one or more detectable labels which are associated with the glucose oxidase molecules and/or the competitor moieties and which are capable of generating an optical signal that changes in a concentration-dependent manner when glucose reversibly binds to the glucose/competitor moiety binding sites; and detecting the optical signal to determine the concentration of glucose in the ocular fluid.

14. The method of claim 13, wherein the competitor moieties are selected from the group consisting of 2-deoxy-D-glucose, D-mannose and D-galactose.

15. The method of claim 14, wherein the competitor moieties are tethered to a polymer meshwork, wherein pores of the polymer meshwork (a) permit glucose to bind reversibly to the glucose/competitor moiety binding sites and (b) prevent the glucose oxidase molecules from diffusing out of the ophthalmic lens.

16. The method of claim 13, wherein at least one of the one or more detectable labels is a fluorescent label.

17. The method of claim 13, wherein the ophthalmic lens is selected from the group consisting of a contact lens, an intraocular lens, a subconjunctival lens, and an intracorneal lens.

18. A method for varying glucose concentration in a body fluid or tissue, comprising the steps of:

contacting an ocular fluid with an ophthalmic lens, wherein the ophthalmic lens comprises competitor moieties; glucose oxidase molecules each of which comprises a glucose/competitor moiety binding site to which glucose and competitor moieties can reversibly bind; and one or more detectable labels which are associated with the glucose oxidase molecules and/or the competitor moieties and which are capable of generating an optical signal that changes in a concentration-dependent manner when glucose reversibly binds to the glucose/competitor moiety binding sites detecting the optical signal to determine the concentration of glucose in the ocular fluid;

transmitting a signal indicating the glucose concentration in the ocular fluid to a pump configured to vary the glucose concentration in the body tissue or fluid; and providing a regulator moiety via the pump to the body tissue or fluid, whereby the glucose concentration in the body tissue or fluid is varied.

19. The method of claim 18, wherein the competitor moieties are selected from the group consisting of 2-deoxy-D-glucose, D-mannose and D-galactose.

20. The method of claim 17, wherein the competitor moieties are tethered to a polymer meshwork, wherein pores of the polymer meshwork (a) permit glucose to bind reversibly to the glucose/competitor moiety binding sites and (b) prevent the glucose oxidase from diffusing out of the ophthalmic lens.

21. The method of claim 18, wherein at least one of the one or more detectable labels is a fluorescent label.

22. The method of claim 18, wherein the regulator moiety is insulin.

23. The method of claim 21, wherein the optical signal is detected by a fluorophotometer.

24. The method of claim 21, wherein the fluorophotometer is contained in a personal accessory.

25. The method of claim 18, wherein the ophthalmic lens is selected from the group consisting of a contact lens, an intraocular lens, a subconjunctival lens, and an intracorneal lens.

* * * * *